(12) United States Patent
Belhe et al.

(10) Patent No.: US 8,273,094 B2
(45) Date of Patent: Sep. 25, 2012

(54) PUNCTURE LOCATING DEVICE

(75) Inventors: Kedar R. Belhe, Minnetonka, MN (US); John Avi Roop, Crystal, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 991 days.

(21) Appl. No.: 11/131,120

(22) Filed: May 17, 2005

(65) Prior Publication Data
US 2006/0264978 A1 Nov. 23, 2006

(51) Int. Cl.
*A61B 17/08* (2006.01)
(52) U.S. Cl. .......................... 606/151; 606/213; 606/153
(58) Field of Classification Search .................. 606/151, 606/213, 139, 153
See application file for complete search history.

(56) References Cited

U.S. PATENT DOCUMENTS

| | | | |
|---|---|---|---|
| 4,317,445 A | 3/1982 | Robinson | |
| 5,061,274 A | 10/1991 | Kensey | |
| 5,222,974 A | 6/1993 | Kensey et al. | |
| 5,282,827 A | 2/1994 | Kensey | |
| 5,304,184 A | 4/1994 | Hathaway | |
| 5,306,254 A | 4/1994 | Nash | |
| 5,403,329 A | 4/1995 | Hinchcliffe | |
| 5,405,354 A | 4/1995 | Sarrett | |
| 5,411,520 A | 5/1995 | Nash et al. | |
| 5,431,639 A * | 7/1995 | Shaw ............................ 604/264 |
| 5,441,517 A | 8/1995 | Kensey et al. | |
| 5,486,195 A | 1/1996 | Myers et al. | |
| 5,496,332 A | 3/1996 | Sierra et al. | |
| 5,613,974 A | 3/1997 | Andreas et al. | |
| 5,662,681 A | 9/1997 | Nash et al. | |
| 5,676,689 A | 10/1997 | Kensey et al. | |
| 5,725,551 A | 3/1998 | Myers et al. | |
| 5,728,132 A | 3/1998 | Van Tassel et al. | |
| 5,755,727 A | 5/1998 | Kontos | |
| 5,855,559 A | 1/1999 | Van Tassel et al. | |
| 5,868,778 A | 2/1999 | Gershony et al. | |
| 6,017,359 A | 1/2000 | Gershony et al. | |
| 6,042,601 A | 3/2000 | Smith | |
| 6,048,357 A | 4/2000 | Kontos | |
| 6,048,358 A | 4/2000 | Barak | |
| 6,110,184 A | 8/2000 | Weadock | |
| 6,136,010 A | 10/2000 | Modesitt et al. | |
| 6,193,670 B1 | 2/2001 | Van Tassel et al. | |
| 6,231,561 B1 | 5/2001 | Frazier et al. | |
| 6,533,762 B2 | 3/2003 | Kanner et al. | |
| 6,682,489 B2 | 1/2004 | Tenerz et al. | |
| 2004/0225301 A1 | 11/2004 | Roop et al. | |

* cited by examiner

*Primary Examiner* — Corrine M McDermott
*Assistant Examiner* — Gregory Anderson
(74) *Attorney, Agent, or Firm* — Holland & Hart LLP

(57) ABSTRACT

Methods and apparatus for locating a device with respect to a blood vessel. An expandable or extrudable member transverse to the device locates an internal surface of a proximal wall of the blood vessel. A typical application of such methods and apparatus is providing relative position between a femoral arterial wall and a closure device axis. Predetermined location positions are recognized as a positive stop transmitted to a physician via tactile feedback.

33 Claims, 4 Drawing Sheets

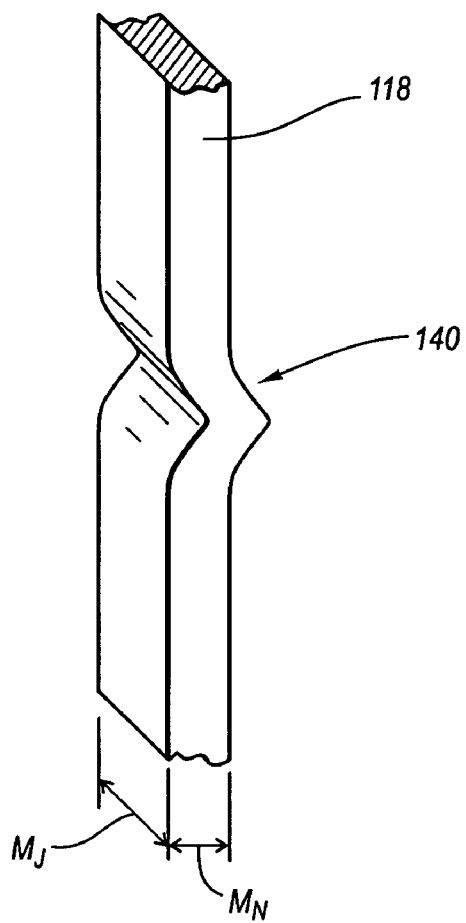
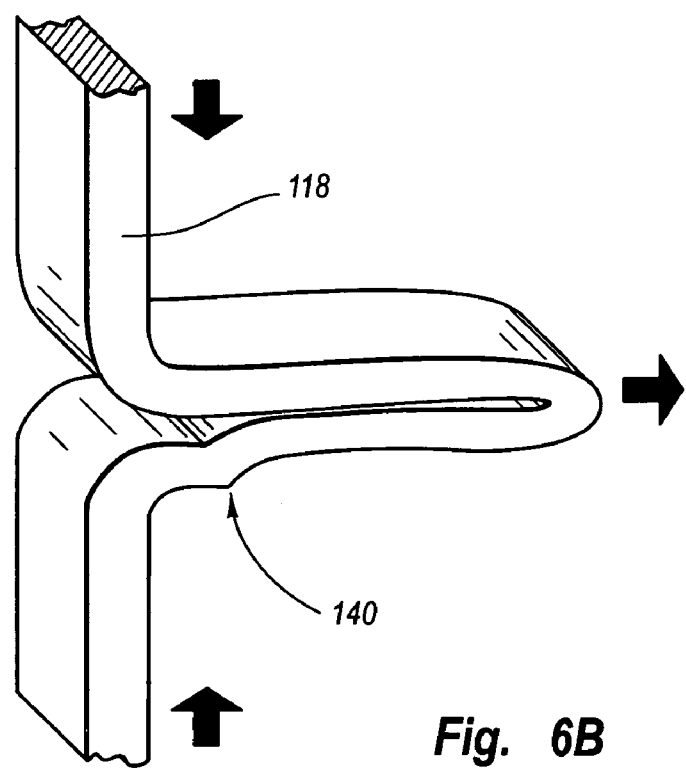
*Fig. 6A*
*Fig. 6B*

PUNCTURE LOCATING DEVICE

FIELD OF THE INVENTION

This invention relates generally to medical devices and more particularly to devices and methods for locating punctures or incisions in an internal tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery. The insertion sheath enables the introduction of other instruments (e.g., a catheter) to an operative position within the vascular system.

Intravascular and intraluminal procedures often include instruments of certain dimensions that must be precisely located with respect to the percutaneous puncture. The relative position of the various instruments with respect to the puncture in the artery must be known by an operator in order to properly conduct the intravascular procedure.

However, intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,863; 6,090,130; and 6,045,569, which are hereby incorporated by this reference. Typical closure devices such as the ones described in the above-mentioned patents place a sealing plug at the tissue puncture site. However, the closure devices must be in a proper position relative to the puncture in order to place the sealing plug. If the location of the puncture relative to the closure device is not precisely known, the sealing plug may not be placed at a location conducive to effecting hemostasis of the puncture.

Typically, location of the puncture within an artery is determined by inserting the closure device and/or an insertion sheath into the artery until blood enters a lumen in the closure device or insertion sheath. As blood exits the lumen through a drip hole in the closure device or insertion sheath, the operator has visual indication of the location of the closure device. The insertion sheath and/or the closure device may then be retracted a certain distance indicated by markings on the insertion sheath to properly locate the closure device relative to the puncture. However, it is sometimes difficult and time consuming for some operators to find the exact location such that blood just begins to flow through a locating lumen, and it can also be inconvenient to monitor the markings on the insertion sheath and retract the closure device and insertion sheath a precise, prescribed distance. Accordingly, it would be helpful to improve the locating method and mechanism such that location could be determined by a positive stop transmitted to an operator by tactile feedback.

SUMMARY

The principles of the present invention facilitate locating or finding relative location of a device with respect to an internal tissue puncture. In one of many possible embodiments, the present invention provides a vascular puncture locator. The vascular puncture locator comprises a tubular member adapted for partial insertion into a blood vessel having first and second ends and a first lumen. The locator also includes a first side port disposed in the tubular member, and a first extrudable member disposed in the first lumen and affixed at a distal end thereof to the first end of the tubular member. The first extrudable member is predisposed to exit through the first side port. A proximal end of the first extrudable member may extend out of the tubular member where it is exposed to an operator. The locator may include a second side port in the tubular member disposed opposite of the first side port. According to some aspects, the second side port in the tubular member is disposed azimuthally in the range of approximately 160-200 degrees from the first side port and spaced axially from the first side port. Therefore, the first and second side ports may lie in a plane at an acute angle from a plane normal to the tubular member at the first side port. The first extrudable member may comprise a super-elastic material such as a nitinol ribbon or other materials. If a ribbon is used, the ribbon may have a major dimension of the same order of magnitude as a major diameter of the tubular member, and a minor dimension an order of magnitude smaller than the major diameter of the tubular member. The extrudable member may be predisposed to bend at a point adjacent to the first side port. A portion of the first extrudable member extends through the first side port to create a transverse foot extending from the tubular member upon compression of a proximal end of the first extrudable member. Accordingly, an operator may retract the tubular member and receive tactile feedback indicating the position of the tubular member with respect to the puncture as the transverse foot engages an inner wall of the blood vessel. According to some embodiments, the tubular member may comprise a vascular puncture closure device.

Another aspect of the invention provides a vascular insertion apparatus. The vascular insertion apparatus comprises a tubular member adapted for insertion into a blood vessel having first and second ends and a first lumen. A first side port is disposed in the tubular member at the first end thereof, which may comprise a lower twenty-five percent portion of the tubular member. The vascular insertion apparatus also includes a first flexible member disposed inside the first lumen and extending across the first side port. The arrangement of the first flexible member across the first side port facilitates extrusion of the first flexible member through the first side port in response to compression of the first flexible member.

The vascular insertion apparatus may further include at least a second side port in the tubular member disposed azimuthally approximately 180 degrees from the first side port. The second side port may be spaced axially from the first side port. Therefore, the first and second side ports may lie in a plane at an acute angle from a plane normal to the tubular member at the first side port. The first flexible member may comprise a super-elastic material having a major dimension of the same order of magnitude as the a major diameter of the tubular member, and a minor dimension an order of magnitude smaller than the major diameter of the tubular member. The first flexible member may be pre-bent or weakened at the first side port. The first flexible member may be extrudable through the first side port to create a transverse foot extending from the tubular member upon compression of a proximal end of the first flexible member, and retractable into the first lumen upon tension of the proximal end.

According to another aspect of the invention there is a method of making a vascular insertion apparatus. The method includes providing a tubular body, disposing an extrudable member into the tubular body, rigidly affixing a distal end of the extrudable member to the tubular body, and providing a first side port in the tubular body receptive of the extrudable member. The method may include predisposing the extrudable member at the first side port to extrude through the side port upon compression of the extrudable member. The predisposing may be accomplished, for example, by pre-bending the extrudable member radially outward at the first side port, weakening the extrudable member by, for example, notching the extrudable member at the first side port, or other methods.

According to some aspects of the invention, the method may include disposing at least a second extrudable member into the tubular body, rigidly affixing a distal end of the second extrudable member to the tubular body, and providing a second side port in the tubular body receptive of the second extrudable member. The second side port may be spaced azimuthally approximately 160-200 degrees and offset axially from the first side port.

Another aspect of the invention provides a method of locating a vascular puncture. The method includes inserting a tubular member into a vessel, extruding a first locating petal transversely through a first side port in the tubular member, retracting the tubular member, and contacting an inner wall of the vessel with the first locating petal. The extruding may comprise compressing an extrudable member, including the first locating petal, along an axis of the tubular member. The method may further include extruding a second locating petal transversely through a second side port in the tubular member and contacting the inner wall of the vessel with the second locating petal. The second side port may be spaced axially from the first side port, and therefore the inserting may comprise inserting at an acute angle between the vessel and the tubular member. If two side ports are included, the method may include extruding a second locating petal transversely through the second side port in the tubular member, the second side port spaced azimuthally opposite of and axially from the first side port, and contacting the inner wall of the vessel with the second locating petal substantially simultaneously with contacting the inner wall of the vessel with the first locating petal.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

FIG. 6A is a perspective view of a locating foot predisposed to bend at a certain point according to one embodiment of the present invention.

FIG. 6B is a perspective view of the locating foot of FIG. 6A after it has been bent according to one embodiment of the present invention.

Throughout the drawings, identical reference numbers designate similar, but not necessarily identical, elements.

DETAILED DESCRIPTION

As mentioned above, vascular procedures are conducted throughout the world and require access to an artery through a puncture. Most often, the artery is a femoral artery. To provide access to the artery and eventually to close the puncture following completion of the procedure, it is important for the operator to know the location of an insertion sheath relative to the puncture. The present invention describes methods and apparatus for locating a vascular puncture relative to a vascular access device. The methods and apparatus indicate location by tactile feedback to an operator. While the vascular instruments shown and described below include particular insertion sheaths, the application of principles described herein to are not limited to the specific devices shown. The principles described herein may be used with any vascular access device. Therefore, while the description below is directed primarily to arterial procedures and certain embodiments of a vascular access device, the methods and apparatus are only limited by the appended claims.

As used throughout the claims and specification the term "lumen" refers to a fluid passageway, for example through a vascular access sheath. A "super-elastic" material refers to material classes that may be elastically strained at least 6%, some of which can elastically strain up to at least 8-10%. "Extrude" or "extrusion" means the act or process of pushing or thrusting out, and does not necessarily mean that the object being extruded (an "extrudable" object) is changing in cross-sectional shape. The words "including" and "having," as used in the specification, including the claims, have the same meaning as the word "comprising."

Figure 1:
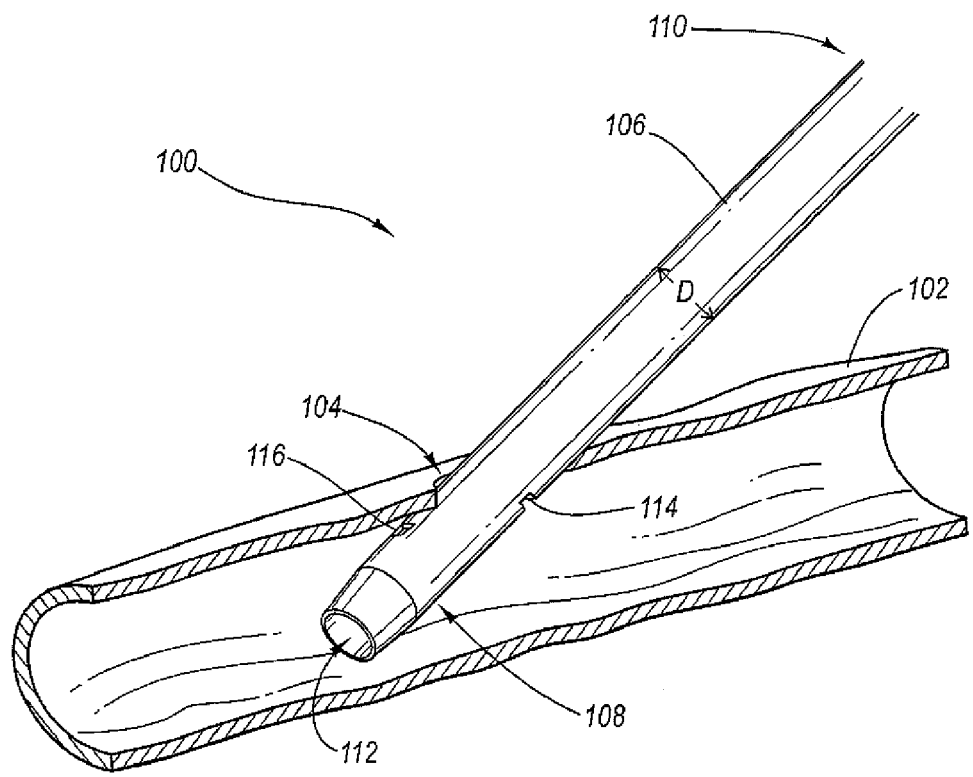
FIG. 1 is a perspective view of a vascular insertion device engaged with an artery, the artery shown in section, according to one embodiment of the present invention.

Referring now to the drawings, and in particular to FIG. 1, a vascular insertion apparatus, for example an insertion sheath 100, is shown according to one embodiment of the present invention. The insertion sheath 100 is shown partially inserted into a blood vessel, which, according to the embodiment of FIG. 1, is an artery 102. The insertion sheath 100 extends through a puncture 104 in the artery 102. The insertion sheath 100 provides access into the artery 102 to any number of vascular instruments and puncture closure devices.

The insertion sheath 100 comprises a tubular member, for example a flexible tubular member 106. The flexible tubular member 106 includes a first or distal end 108, a second or proximal end 110, and a sidewall 109. The flexible tubular member 106 defines a first internal lumen or central inner bore 112 receptive of vascular instruments and closure devices. The flexible tubular member 106 has a major diameter indicated by D in FIG. 1, and may be on the order of 0.1 inches. The insertion sheath 100 includes at least one side port disposed in the sidewall 109 of the flexible tubular member 106. As shown in FIG. 1, the flexible tubular member 106 includes a first side port 114 and a second side port 116 that facilitate locating the insertion sheath 100 relative to the puncture 104. The advantages of the first and second side port 114, 116 for locating the puncture 104 are discussed in more detail below.

Figure 2:
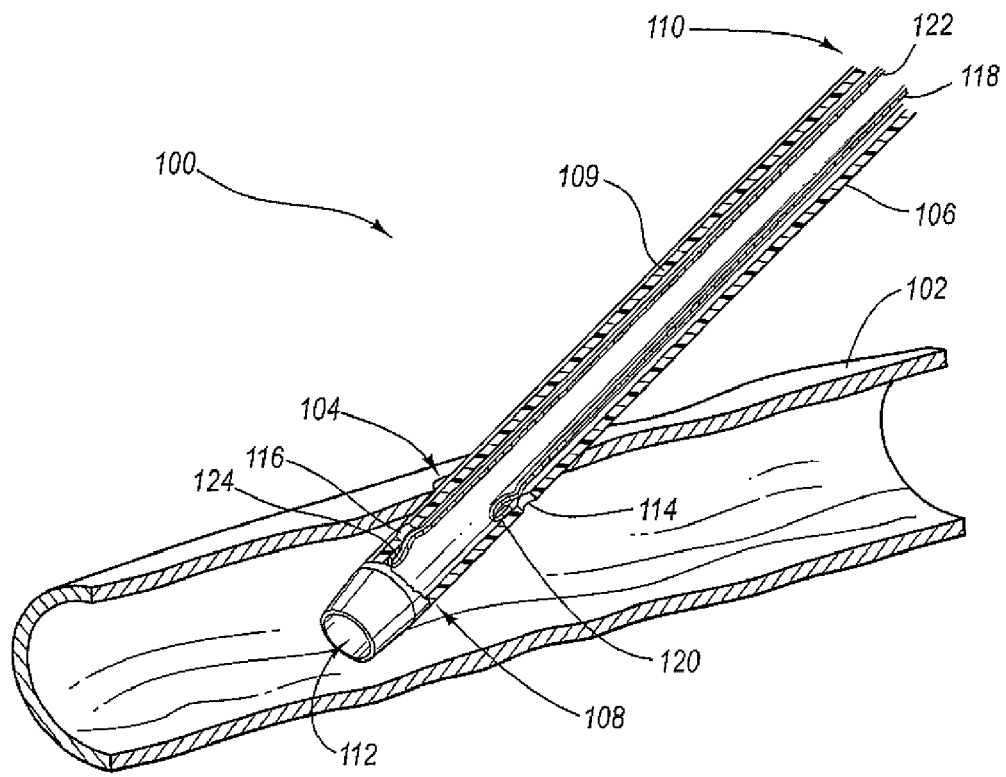
FIG. 2 is a perspective view, partly in section, of the vascular insertion device shown in FIG. 1 engaged with the artery according to one embodiment of the present invention.

Referring next to FIG. 2, a first extrudable member is disposed in the first lumen 112. The first extrudable member is a first super elastic ribbon 118 according to FIG. 2. The super elastic ribbon 118 may comprise nitinol or other super elastic materials. The first super elastic ribbon 118 is affixed at a distal end 120 to the first end 108 of the flexible tubular member 106. The distal end 120 of the first super elastic ribbon 118 may be affixed to the flexible tubular member 106 by adhesive, welding, or any other affixing method. The distal end 120 of the first super elastic ribbon 118 is affixed to an inner surface of the flexible tubular member 106 distal of and adjacent to the first side port 114. In addition, the first super elastic ribbon 118 is preferably azimuthally aligned with the first side port 114. Therefore, the first super elastic ribbon 118 extends across the first side port 114.

The insertion sheath 100 may also comprise a second extrudable member such as a second super elastic ribbon 122. The second super elastic ribbon 122 may also comprise nitinol. The second super elastic ribbon 122 is affixed at a distal end 124 to the flexible tubular member 106 in a manner similar or identical to the attachment between the first super elastic ribbon 118 and the flexible tubular member 106. The distal end 124 of the second super elastic ribbon 122 is affixed to the flexible tubular member 106 distal of the second side port 116. In addition, the second super elastic ribbon 122 is preferably azimuthally aligned with the second side port 116. Therefore, the second super elastic ribbon 122 extends across the second side port 116. The first and second super elastic ribbons 118, 122 extend proximally to free ends that are discussed below with reference to FIG. 3.

Figure 3:
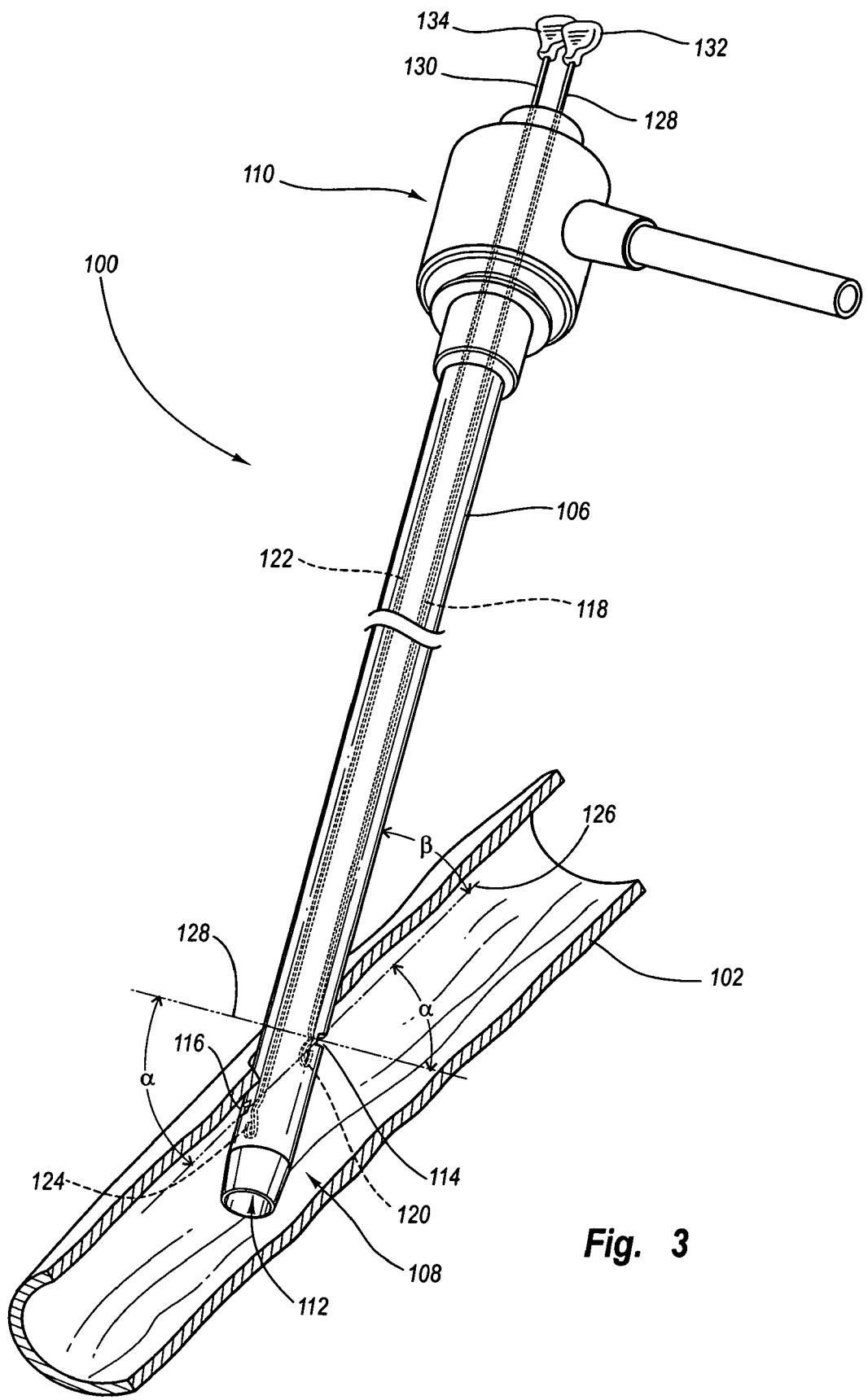
FIG. 3 is a perspective view of the vascular insertion device shown in FIG. 1, illustrating a proximal end of the device according to one embodiment of the present invention.

As shown in FIG. 3, the first and second side ports 114, 116 are preferably spaced from one another azimuthally. The first and second side ports 114, 116 may be spaced azimuthally from one another by approximately 100-300 radial degrees, more preferably by approximately 160-200 radial degrees, and most preferably by approximately 180 degrees such that the first and second side ports 114, 116 are arranged opposite of one another. In addition, the first and second side ports 114, 116 are preferably spaced from one another axially. For example, as shown in FIG. 3, according to some embodiments of the present invention, the first and second side ports 114, 116 lie in a plane 126 at an acute angle α from a plane 128 normal to the flexible tubular member 106. The acute angle β is preferably within twenty percent or substantially equal to an angle β at which the insertion sheath 100 is typically inserted relative to the artery 102.

Figure 4:
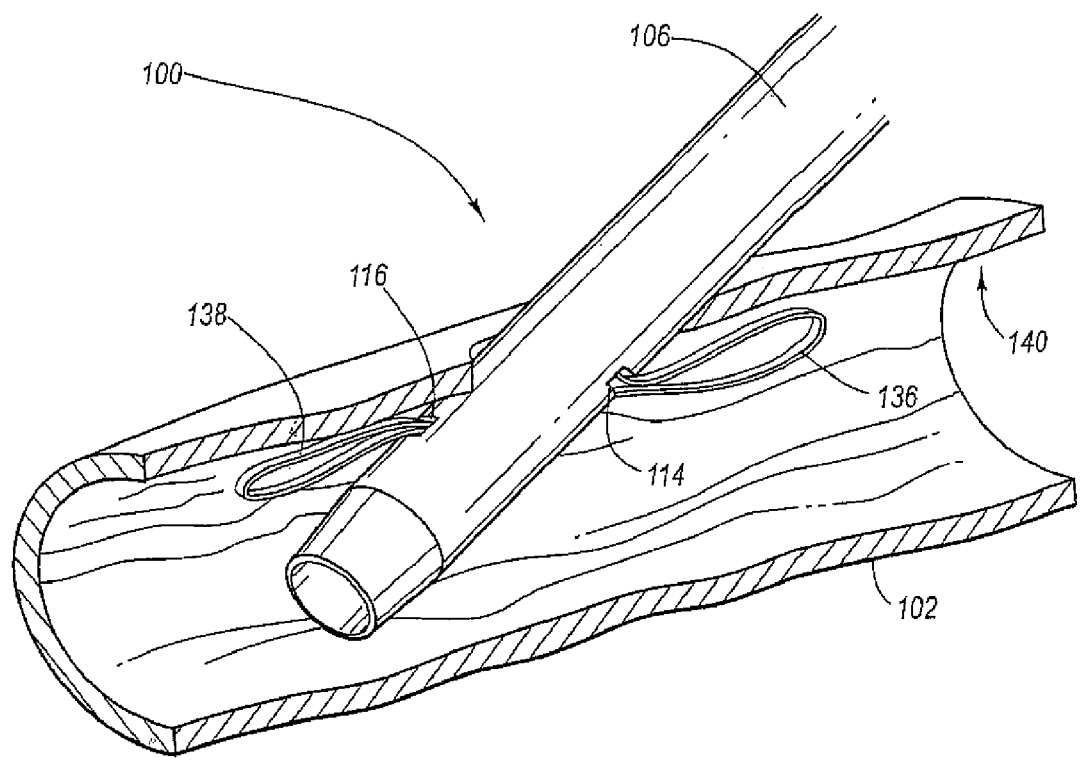
FIG. 4 is a perspective view of the vascular insertion device shown in FIG. 1, with locating feet deployed according to one embodiment of the present invention.

The first and second super elastic ribbons 118, 122 each extend proximally to first and second free ends 128, 130, respectively. The first free end 128 may be attached to a first tab 132 and the second free end 130 may be attached to a similar or identical second tab 134. The first and second tabs 132, 134 are accessible to an operator, allowing the operator to apply pressure to the first and second super elastic ribbons 118, 122 and place the super elastic ribbons in compression. Accordingly, with the insertion sheath 100 placed inside the artery 102 as shown in FIG. 3, an operator may apply pressure to the first and second tabs 132, 134 to buckle and extrude the first and second super elastic ribbons 118, 122 through the first and second associated side ports 114, 116 as shown in FIG. 4. The first and second super elastic ribbons 118, 122 (FIG. 3) therefore may act as columns, which will buckle when a critical load is reached.

Figure 5:
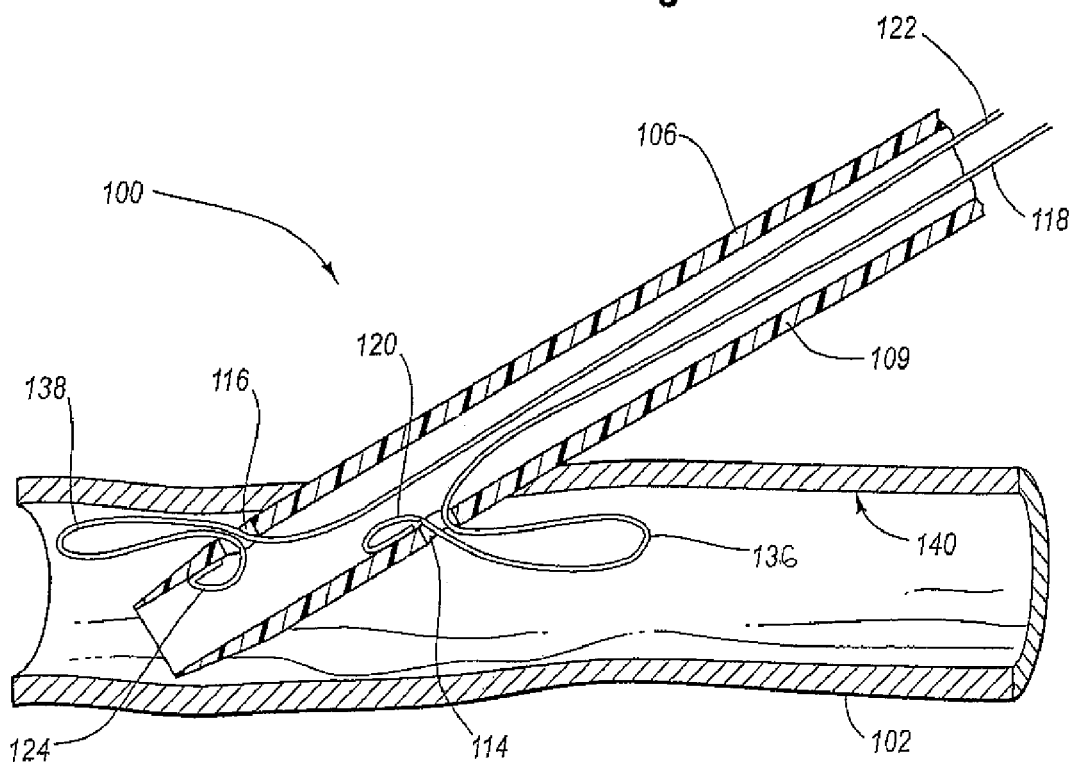
FIG. 5 is a cross-sectional view of the vascular insertion device shown in FIG. 4.

As the first and second super elastic ribbons 118, 122 (FIG. 3) buckle and extrude through the first and second side ports 114, 116, they form first and second feet or petals 136, 138, respectively, as shown in FIGS. 4-5. The first and second feet 136, 138 preferably extend substantially parallel to an inner wall 140 of the artery 102 because the first and second ports 114, 116 are offset axially. The first and second feet 136, 138 act as stops and provide tactile feedback to the operator as the insertion sheath 100 is retracted, which results in contact between the first and second feet 136, 138 and the inner wall 140. Accordingly, the location of the insertion sheath 100 relative to the puncture 104 may be accurately determined by the operator when the operator feels the first and/or second feet 136, 138 contact the inner wall 140. Various vascular instruments or puncture closure devices may then be properly introduced through the insertion sheath 100.

When the operator desires to remove the insertion sheath 100 from the puncture 104, the first and second feet 136, 138 may be retracted back within the insertion sheath. The first and second feet 136, 138 are retracted by pulling on the tabs 132, 134 (FIG. 3) or otherwise placing the first and second super elastic ribbons 118, 122 in tension.

According to some embodiments, the first and second super elastic ribbons 118, 122 are predisposed to buckle at the first and second side ports 114, 116, respectively. Therefore, as shown in FIGS. 6A-6B, the first super elastic ribbon 118 may be weakened at a point adjacent to the first side port 114 (FIG. 1). FIGS. 6A-6B illustrate only the first super elastic ribbon 118, but the second super elastic ribbon 122 (FIG. 2) may be similarly weakened (although in an opposite direction or mirror image). As shown in FIG. 6A, the super elastic ribbon 118 may include a pre-bend, notch 140 or other controlled weakening mechanism adjacent to the first side port 114. Therefore, as the super elastic ribbon 118 is placed in compression, it will tend to buckle at the notch 140 and extrude or exit through the side port 114 (FIG. 5). FIG. 6B illustrates the forces on the super elastic ribbon 118 as it is placed in compression and extrudes through the first side port 114 (FIG. 5).

According to the embodiment of FIGS. 6A-6B, the dimensions of the super elastic ribbon 118 are shown. According to some embodiments, a major dimension $M_J$ of the super elastic ribbon 118 is of the same order of magnitude as the major diameter D (FIG. 1) of the flexible tubular member 106 (FIG. 1). A minor dimension $M_N$ of the super elastic ribbon 118 may be an order of magnitude smaller than the major diameter D (FIG. 1) of the flexible tubular member 106 (FIG. 1). The combination of the major dimension $M_J$ being of the same order of magnitude as the major diameter D (FIG. 1) and the minor dimension $M_N$ being an order of magnitude smaller than the major diameter D (FIG. 1) facilitates the extrusion of the super elastic ribbon 118 through the first side port 114 (FIG. 5). However, the first super elastic ribbon may comprise other dimensions as well. The second super elastic ribbon 122 (FIG. 5) preferably has similar or identical dimensions to the first super elastic ribbon 118.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A vascular puncture locator, comprising:
   a tubular member configured as an introducer and adapted for partial insertion into a blood vessel, the tubular member having first and second ends, a sidewall defining an exterior surface, and a central inner bore that extends from the first end to the second end and defines an interior surface, the inner bore being receptive of vascular instruments and closure devices;
   a first side port disposed in the sidewall of the tubular member and extending from the inner bore through the sidewall to the exterior surface of the tubular member;

a first extrudable member disposed inside the inner bore proximal of the first side port and directly affixed at a distal end thereof to the interior surface at the first end of the tubular member;

wherein the first extrudable member is predisposed to exit through the first side port in a lateral direction from the inner bore to the exterior surface.

2. A vascular puncture locator according to claim 1 wherein a proximal end of the first extrudable member extends out of the inner bore of the tubular member at the second end and is exposed to an operator.

3. A vascular puncture locator according to claim 1, further comprising a second side port in the tubular member extending from the inner bore to the exterior surface of the tubular member and disposed opposite of the first side port.

4. A vascular puncture locator according to claim 1, further comprising a second side port in the tubular member extending from the inner bore to the exterior surface of the tubular member and disposed azimuthally approximately 160-200 degrees from the first side port and spaced axially from the first side port.

5. A vascular puncture locator according to claim 1, further comprising a second side port in the tubular member extending from the inner bore to the exterior surface of the tubular member and disposed azimuthally approximately 160-200 degrees from the first side port and spaced axially from the first side port such that the first and second side ports lie in a plane at an acute angle from a plane normal to the tubular member at the first side port.

6. A vascular puncture locator according to claim 1 wherein the first extrudable member comprises a super-elastic material.

7. A vascular puncture locator according to claim 1 wherein the first extrudable member comprises a ribbon having a major dimension of the same order of magnitude as a major diameter of the tubular member, and a minor dimension an order of magnitude smaller than the major diameter of the tubular member.

8. A vascular puncture locator according to claim 1 wherein the first extrudable member comprises a nitinol ribbon.

9. A vascular puncture locator according to claim 1 wherein the first extrudable member is predisposed to bend at a point adjacent to the first side port.

10. A vascular puncture locator according to claim 1 wherein a portion of the first extrudable member extends through the first side port to create a transverse foot extending from the tubular member upon compression of a proximal end of the first extrudable member.

11. A vascular puncture locator according to claim 1, wherein the tubular member comprises a vascular puncture closure device.

12. A vascular puncture locator according to claim 1 wherein the inner bore is receptive of vascular instruments and closure devices.

13. A vascular puncture locator according to claim 1 the first extrudable member being affixed to the interior surface adjacent the first side port.

14. A vascular insertion apparatus, comprising:
a tubular member configured as an introducer and adapted for insertion into a blood vessel, the tubular member having first and second ends, a sidewall that defines an exterior surface, and a central inner bore that extends from the first end to the second end and defines an interior surface, the inner bore being receptive of vascular instruments and closure devices;

a first side port disposed in the sidewall of the tubular member and extending from the inner bore through the sidewall to the exterior surface of the tubular member;

a first flexible member disposed inside the inner bore proximal of the first side port and extending across the first side port, the first flexible member being affixed to the interior surface at a location distal of the first side port;

wherein compression of the first flexible member effects extrusion thereof through the first side port in a lateral direction from the inner bore to the exterior surface.

15. A vascular insertion apparatus according to claim 14, further comprising a second side port in the tubular member extending from the inner bore to the exterior surface of the tubular member and disposed azimuthally approximately 180 degrees from the first side port.

16. A vascular insertion apparatus according to claim 14, further comprising a second side port in the tubular member extending from the inner bore to the exterior surface of the tubular member and disposed azimuthally approximately 160-200 degrees from the first side port and spaced axially from the first side port.

17. A vascular insertion apparatus according to claim 14, further comprising a second side port in the tubular member extending from the inner bore to the exterior surface of the tubular member and disposed azimuthally approximately 160-200 degrees from the first side port and spaced axially from the first side port such that the first and second side ports lie in a plane at an acute angle from a plane normal to the tubular member at the first side port.

18. A vascular insertion apparatus according to claim 14 wherein the first flexible member comprises a super-elastic material having a major dimension of the same order of magnitude as a major diameter of the tubular member, and a minor dimension an order of magnitude smaller than the major diameter of the tubular member.

19. A vascular insertion apparatus according to claim 14 wherein the first flexible member comprises a nitinol ribbon.

20. A vascular insertion apparatus according to claim 14 wherein the first flexible member is pre-bent at the first side port.

21. A vascular insertion apparatus according to claim 14 wherein the first flexible member is extrudable through the first side port to create a transverse foot extending from the tubular member.

22. A vascular insertion apparatus according to claim 14 wherein the first flexible member is extrudable through the first side port to create a transverse foot extending from the tubular member upon compression of a proximal end of the first flexible member, and retractable into the first lumen upon tension of the proximal end.

23. A method of making a vascular insertion apparatus, comprising:
providing a tubular body having first and second ends, a sidewall defining an exterior surface, and a central inner bore that extends from the first end to the second end and defines an interior surface, the inner bore being receptive of vascular instruments and closure devices;

disposing an extrudable member into the inner bore of the tubular body;

rigidly affixing a distal end of the extrudable member to the interior surface of the tubular body within the inner bore;

providing a first side port in the tubular body receptive of extrudable member, the first side port extending from the inner bore interior through the sidewall to the exterior surface of the tubular body, the extrudable member positioned inside the inner bore proximal of the first side port and being extrudable through the first side port in a lateral direction from the inner bore to the exterior surface.

24. A method of making a vascular insertion apparatus according to claim 23, further comprising predisposing the extrudable member at the first side port to extrude through the side port upon compression of the extrudable member.

25. A method of making a vascular insertion apparatus according to claim 23, further comprising pre-bending the extrudable member radially outward at the first side port.

26. A method of making a vascular insertion apparatus according to claim 23, further comprising:
disposing at least a second extrudable member into the inner bore of the tubular body;
rigidly affixing a distal end of the second extrudable member to the tubular body within the inner bore;
providing a second side port in the tubular body receptive of the second extrudable member, the second side port extending from the inner bore to the exterior surface of the tubular body.

27. A method of making a vascular insertion apparatus according to claim 23, further comprising:
disposing at least a second extrudable member into the inner bore of the tubular body;
rigidly affixing a distal end of the second extrudable member to the tubular body within the inner bore;
providing a second side port in the tubular member receptive of the second extrudable member at approximately 160-200 degrees from the first side port, the second side port extending from the inner bore to the exterior surface of the tubular body.

28. A method of making a vascular insertion apparatus according to claim 23, further comprising:
disposing at least a second extrudable member into the inner bore of the tubular body;
rigidly affixing a distal end of the second extrudable member to the tubular body within the inner bore;
providing a second side port in the tubular member receptive of the second extrudable member at approximately 160-200 degrees from the first side port and offset axially from the first side port, the second side port extending from the inner bore to the exterior surface of the tubular body.

29. A method of locating a vascular puncture, comprising:
inserting a tubular member into a vessel, the tubular member being configured as an introducer and including a first end, a second end, a sidewall defining an exterior surface, a central inner bore extending from the first end to the second end and defining an interior surface, and a first side port defined in the sidewall, the inner bore being receptive of vascular instruments and closure devices;
extruding a first locating petal of an extrudable member transversely through the first side port in the tubular member from the inner bore to the exterior surface, the first side port extending from the inner bore defined in the tubular member through the sidewall to the exterior surface of the tubular member, a portion of the extrudable member positioned within the inner bore proximal of the first side port and being affixed to the interior surface;
retracting the tubular member;
contacting an inner wall of the vessel with the first locating petal.

30. A method of locating a vascular puncture according to claim 29 wherein the extruding comprises compressing the extrudable member including the first locating petal along an axis of the tubular member.

31. A method of locating a vascular puncture according to claim 29, further comprising:
extruding a second locating petal transversely through a second side port in the tubular member, the second side port extending from the inner bore to the exterior surface of the tubular member;
contacting the inner wall of the vessel with the second locating petal.

32. A method of locating a vascular puncture according to claim 29, further comprising:
extruding a second locating petal transversely through a second side port in the tubular member, the second side port spaced axially from the first side port and extending from the inner bore to the exterior surface of the tubular member.

33. A method of locating a vascular puncture according to claim 29 wherein the inserting comprises inserting at an acute angle between the vessel and the tubular member, and further comprising:
extruding a second locating petal transversely through a second side port in the tubular member, the second side port spaced azimuthally opposite of and axially from the first side port and extending from the inner bore to the exterior surface of the tubular member;
contacting the inner wall of the vessel with the second locating petal substantially simultaneously with contacting the inner wall of the vessel with the first locating petal.

* * * * *